United States Patent
Fukao et al.

(10) Patent No.: US 7,449,600 B2
(45) Date of Patent: Nov. 11, 2008

(54) PROCESS FOR PRODUCING CYCLOHEXANONE OXIME

(75) Inventors: Masami Fukao, Ritto (JP); Shinichi Kawase, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/360,631

(22) Filed: Feb. 24, 2006

(65) Prior Publication Data

US 2006/0205939 A1 Sep. 14, 2006

(30) Foreign Application Priority Data

Feb. 28, 2005 (JP) ............... 2005-052876

(51) Int. Cl.
*C07C 277/00* (2006.01)

(52) U.S. Cl. ...................... 564/267; 540/535

(58) Field of Classification Search ........... 564/267; 540/535

See application file for complete search history.

(56) References Cited

U.S. PATENT DOCUMENTS

| | | | |
|---|---|---|---|
| 4,410,501 A | | 10/1983 | Taramasso et al. |
| 4,745,221 A | | 5/1988 | Roffia et al. |
| 5,227,525 A | * | 7/1993 | Tonti et al. .......... 564/267 |
| 5,312,987 A | | 5/1994 | Mantegazza et al. |
| 2005/0119479 A1 | * | 6/2005 | Fukao et al. .......... 540/535 |

FOREIGN PATENT DOCUMENTS

| | | | |
|---|---|---|---|
| EP | 0496385 | A1 | 7/1992 |
| EP | 0564040 | A2 | 10/1993 |
| GB | 977812 | * | 11/1962 |
| GB | 1056124 | * | 6/1964 |
| JP | 62-59256 | A | 3/1987 |
| JP | 6-49015 | A | 2/1994 |
| JP | 6-92922 | A | 4/1994 |

* cited by examiner

*Primary Examiner*—Janet L. Andres
*Assistant Examiner*—Sudhakar Katakam
(74) *Attorney, Agent, or Firm*—Birch, Stewart, Kolasch & Birch, LLP

(57) ABSTRACT

A process for producing cyclohexanone oxime is provided: (1) reacting cyclohexanone, hydrogen peroxide and ammonia in the presence of a titanosilicate catalyst to give a reaction solution containing cyclohexanone oxime, water, unreacted ammonia and unreacted cyclohexanone, (2) distilling off ammonia, (3) an extraction step, (4) mixing the organic layer obtained in step (3) with water followed by separating into an organic and aqueous layers, (5) distilling off organic solvent and water to obtain a bottom product containing cyclohexanone oxime and cyclohexanone, and (6) distilling off cyclohexanone and to obtain a bottom product containing cyclohexanone oxime; wherein a compound selected from an oxide, an oxo acid, an oxo acid salt, an oxo acid ester and an oxo acid amide of boron or phosphorous is added to at least one of the water used in the step (4) and the organic layer obtained in step (4) to be subjected to step (5).

6 Claims, 1 Drawing Sheet

(A)                                    (B)

PROCESS FOR PRODUCING CYCLOHEXANONE OXIME

BACKGROUND OF THE INVENTION

1. Technical Field

The present invention relates to a process for producing cyclohexanone oxime. Cyclohexanone oxime is useful as a raw material of ε-caprolactam and further, a raw material of nylon-6, and the like.

2. Description of the Related Art

As a process for producing cyclohexanone oxime, a process wherein an ammoximation reaction of cyclohexanone is carried out with hydrogen peroxide and ammonia in the presence of a titanosilicate catalyst has been known (see for example, JP-A-62-59256 (1987), JP-A-6-49015 (1994) and JP-A-6-92922 (1994)). With respect to a process for collecting cyclohexanone oxime from a reaction solution which has been obtained by the ammoximation reaction, for example, JP-A-62-59256 (1987) discloses a process wherein the above-mentioned ammoximation reaction is carried out using water as a reaction solvent and cyclohexanone oxime is extracted with toluene from the reaction solution after removing the catalyst from the solution by filtration. Further, JP-A-6-92922 (1994) discloses a process which includes carrying out the above-mentioned ammoximation reaction using a mixed solvent of t-butyl alcohol and water as the reaction solvent, subjecting the reaction solution from which the catalyst has been removed by filtration to distillation to remove unreacted ammonia and water-containing t-butyl alcohol as distillate, and extracting cyclohexanone oxime with toluene from the bottom product, and then subjecting the extract to distillation to remove toluene as distillate, and collecting cyclohexanone oxime as a bottom product.

SUMMARY OF THE INVENTION

However, the thermal stability of cyclohexanone oxime which is collected according to the above-mentioned conventional processes is not always adequate. For this reason, there are a problem caused by generation of a tar and problems of reduction in yield and deterioration in quality, for example, when the collected cyclohexanone oxime is stored and transferred in a heated and melted state, and when the collected cyclohexanone oxime is gasified for purification by distillation or for the Beckmann rearrangement reaction.

Then, the present inventors have intensively studied for the purpose of developing a process for advantageously collecting cyclohexanone oxime superior in thermal stability, in a process for producing cyclohexanone oxime by the above-mentioned ammoximation reaction. As a result, the inventors have found that the above-mentioned purpose can be attained by carrying out the ammoximation reaction and then subjecting said reaction solution to a series of steps consisting of predetermined distillation, extraction and washing, to complete the present invention.

The present invention is to provide a process for producing cyclohexanone oxime which includes the following steps (1) to (6);

(1) reaction step: a step of reacting cyclohexanone, hydrogen peroxide and ammonia in the presence of a titanosilicate catalyst to give a reaction solution containing cyclohexanone oxime, water, unreacted ammonia and unreacted cyclohexanone, (2) first distillation step: a step of subjecting the reaction solution obtained in the step (1) to distillation to distil off ammonia and obtain a bottom product containing cyclohexanone oxime, water and cyclohexanone, (3) extraction step: a step of mixing the bottom product obtained in the step (2) with an organic solvent followed by separating a mixture into an organic layer and an aqueous layer, (4) washing step: a step of mixing the organic layer obtained in the step (3) with water followed by separating a mixture into an organic layer and an aqueous layer, (5) second distillation step: a step of subjecting the organic layer obtained in the step (4) to distillation to distill off the organic solvent and water and to obtain a bottom product containing cyclohexanone oxime and cyclohexanone, and (6) third distillation step: a step of subjecting the bottom product obtained in the step (5) to distillation to distil off cyclohexanone and to obtain a bottom product containing cyclohexanone oxime;

wherein a compound selected from an oxide, an oxo acid, an oxo acid salt, an oxo acid ester and an oxo acid amide of boron or phosphorous is added to at least one of the water used in the step (4) and the organic layer obtained in the step (4) to be subjected to the step (5).

In this production process, the ammonia distilled off in the first distillation step (2) is desirably recycled as ammonia used in the reaction step (1). Further, the organic solvent distilled off in the second distillation step (5) is desirably recycled as the organic solvent used in the extraction step (3), and the water distilled off in the second distillation step (5) is desirably recycled as water used in the washing step (4). Furthermore, the cyclohexanone distilled off in the third distillation step (6) is desirably recycled as cyclohexanone used in the reaction step (1).

According to the present invention, cyclohexanone oxime superior in thermal stability can be advantageously produced.

Figure 1:
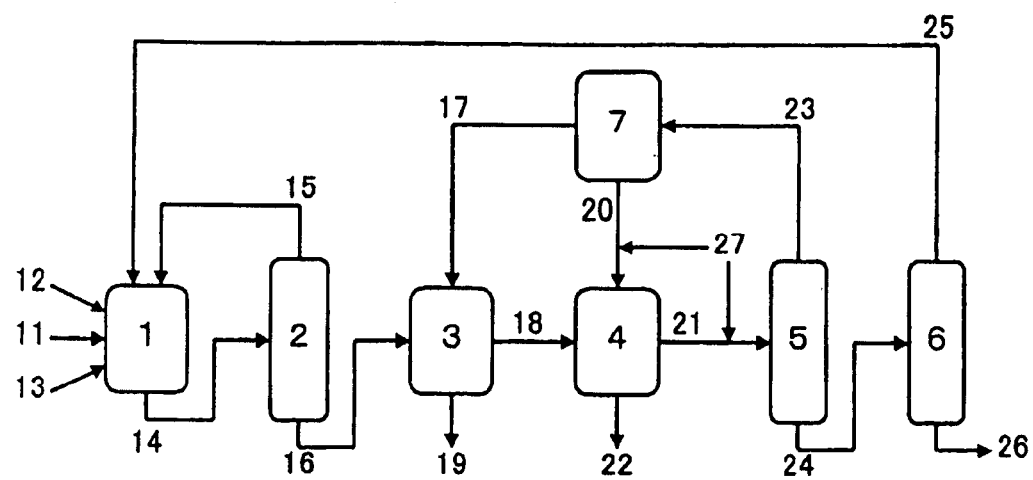
FIG. 1 is a flow chart schematically showing an example of a continuous production process of cyclohexanone oxime according to the present invention.

In the drawings, the numerals indicate the following members, respectively:

1 . . . reactor
2 . . . first distillation column
3 . . . extractor
4 . . . washer
5 . . . second distillation column
6 . . . third distillation column
7 . . . liquid/liquid separator
8 . . . collector
11 . . . cyclohexanone
12 . . . hydrogen peroxide
13 . . . ammonia
17 . . . organic solvent
20 . . . water
24 . . . crude cyclohexanone oxime
26 . . . purified cyclohexanone oxime
27 . . . a compound of boron or phosphorous

DETAILED DESCRIPTION OF THE INVENTION

The present invention is described in detail with reference to the attached drawings. The process for producing cyclohexanone oxime of the present invention consists of a series of steps which include (1) a reaction step wherein the ammoximation reaction of cyclohexanone with hydrogen peroxide and ammonia is carried out in the presence of a titanosilicate catalyst to give a reaction solution, (2) a first distillation step wherein residual ammonia is distilled off from the reaction solution and a cyclohexanone oxime/water-mixed solution (including unreacted cyclohexanone) is obtained as a bottom product, (3) an extraction step wherein cyclohexanone oxime (including unreacted cyclohexanone) is extracted with an organic solvent from the cyclohexanone oxime/water-mixed solution, (4) a washing step wherein an extract containing cyclohexanone oxime is washed with water, (5) a second distillation step wherein the organic solvent is distilled off from the extract containing cyclohexanone oxime which has been washed, to obtain crude cyclohexanone oxime, and (6) a third distillation step wherein residual cyclohexanone is distilled off from the crude cyclohexanone oxime and pure cyclohexanone oxime is obtained as a bottom product. In addition, the present invention requires adding a compound selected from an oxide, an oxo acid, an oxo acid salt, an oxo acid ester and an oxo acid amide of boron or phosphorous to one of or both of the water used in the washing step (4) and the washed cyclohexanone oxime extract to be subjected to the second distillation step (5) in order to sufficiently increase thermal stability of the purified cyclohexanone oxime. All of these steps may be carried out in a continuous operation. Alternatively, a part of the steps may be carried out in a continuous operation and the other part of them may be carried out in batch operations. Alternatively, all of them may be carried out in batch operations. However, it is preferable that all steps are carried out in a continuous operation from the viewpoints of productivity of cyclohexanone oxime and the thermal stability and quality of cyclohexanone oxime obtained by this process.

FIG. 1 is a flow chart schematically showing an embodiment of a continuous production process of cyclohexanone oxime according to the present invention. In this process, firstly, a predetermined amount of the reaction solution with the catalyst dispersed therein is held in a reaction vessel 1. The ammoximation reaction is conducted by feeding cyclohexanone 11, hydrogen peroxide 12, ammonia 13, and a solvent if necessary in the reaction solution while drawing the reaction solution 14 whose amount is substantially equal to those of the raw materials (reaction step (1)). Here, the reaction solution 14 is preferably drawn such that only its liquid phase is drawn through a filter or the like, and the catalyst remains in the reaction vessel 1. When the catalyst is simultaneously drawn, a step of separating the catalyst from the drawn reaction solution 14 is required and the catalyst is required to be fed to the reaction vessel 1. The concentration of the catalyst depends on the activity, reaction conditions and the like, and is usually within a range of 1 g/L to 200 g/L, when the concentration is indicated as the weight per the volume of the reaction solution (catalyst+liquid phase). Further, the reaction vessel 1 is preferably glass-lined one or made of stainless steel from the viewpoint of prevention of the decomposition of hydrogen peroxide.

The titanosilicate used as a catalyst may be one including titanium, silicon and oxygen as elements which constitute the skeleton, which may be one in which the skeleton is constituted by substantially only titanium, silicon and oxygen or one in which further includes other elements as elements which constitute the skeleton. The titanosilicate preferably has an atom ratio of silicon/titanium of 10 to 1000, and the shape thereof may be, for example, in the form of fine powder or pellets. The titanosilicate can be prepared, for example, according to a method disclosed in JP-A-56-96720.

The amount of hydrogen peroxide is usually from 0.5 to 3-fold by mol, and preferably from 0.5 to 1.5-fold by mol based on the moles of cyclohexanone. Further, the amount of ammonia is usually 1-fold by mol or more and preferably 1.5-fold by mol or more based on the moles of cyclohexanone. Ammonia is used in a more excessive amount than that of cyclohexanone and hydrogen peroxide so as to reside in the reaction solution and thereby, the conversion of cyclohexanone and the selectivity of cyclohexanone oxime are enhanced.

Preferable solvents used in the reaction step (1) include, for example, alcohols such as methyl alcohol, ethyl alcohol, n-propyl alcohol, isopropyl alcohol, n-butyl alcohol, sec-butyl alcohol, tert-butyl alcohol and tert-amyl alcohol, water and a mixed solvent thereof.

The reaction temperature is usually within a range of 50° C. to 120° C., and preferably within a range of 70° C. to 100° C. Further, the reaction is preferably carried out under pressure for enhancing the solubility of ammonia in the reaction solution.

In the reaction solution 14 thus obtained, water which is produced by the reaction is theoretically contained in an amount of 2-fold by mol based on the moles of cyclohexanone, together with the objective cyclohexanone oxime ($C_6H_{10}O+NH_3+H_2O_2 \rightarrow C_6H_{10}NOH+2H_2O$). Further, since hydrogen peroxide is usually used in a form of a 10-70 wt % $H_2O_2$ containing aqueous solution, the water in this solution is also contained in the reaction solution 14. Further, since ammonia is excessively used as described above, unreacted ammonia is also contained in the reaction solution 14. Furthermore, since it is difficult for cyclohexanone to completely react, unreacted cyclohexanone is also contained in the reaction solution 14.

Next, the reaction solution 14 containing cyclohexanone oxime, water, ammonia and cyclohexanone is introduced in a first distillation column 2 to be subjected to distillation, ammonia is collected as a distillate 15, and a mixture of cyclohexanone oxime, water and cyclohexanone is obtained as the a bottom product 16 (the first distillation step 2). The distillation is usually carried out under normal pressure and may be carried out under pressure or under reduced pressure, if necessary.

Ammonia collected as the distillate 15 is desirably recycled to the reaction vessel 1. Further, when an organic solvent is used in the reaction step (1), that is, when an organic solvent is fed to the reaction vessel 1, the organic solvent is contained in the reaction solution 14 and introduced into the first distillation column 2. It is desirable that also this organic solvent is collected as the distillate 15 and recycled to the reaction vessel 1. The organic solvent used in the reaction step (1) is required to have a lower boiling point than that of cyclohexanone oxime in order to recycle also the organic solvent to the reaction vessel 1. Some of organic solvents are distilled off accompanying water as an azeotrope or the like. In that case, the water may be also recycled together with the organic solvent to the reaction vessel 1. For example, since tert-butyl alcohol is distilled off as water-containing tert-butyl alcohol containing water in an amount of 12% to 18% by weight, the water-containing t-butyl alcohol may be recycled to the reaction vessel 1. Ammonia is usually recycled to the reaction vessel 1 in a gaseous form using a compressor. Alternatively, ammonia may be recycled to the reaction vessel 1 as a solution by being cooled to a low temperature under pressure and dissolved in an organic solvent or an organic solvent containing water.

The bottom product 16 drawn from the first distillation column 2 is introduced in an extractor 3 followed by being mixed with an organic solvent 17, and then the mixture is separated into an organic layer 18 containing cyclohexanone oxime and cyclohexanone which are extracted from the bottom product 16 with the organic solvent and an aqueous layer 19 which is a raffinate (the extraction step (3)). The organic solvent 17 for extraction is required to be able to be separated from water, to have capability of dissolving cyclohexanone oxime and to have a lower boiling point than that of cyclohexanone oxime. Suitable examples of the organic solvents include an aromatic hydrocarbon solvent such as toluene, an alicyclic hydrocarbon solvent such as cyclohexane, an aliphatic hydrocarbon solvent such as hexane and heptane, an ether such as diisopropyl ether and tert-butylmethyl ether, an ester such as ethyl acetate and the like. The hydrocarbon solvents such as toluene, cyclohexane and heptane are preferable and the aromatic hydrocarbon solvent such as toluene is particularly preferable. The amount of the organic solvent 17 is usually from 0.1 to 2-fold by weight, and preferably from 0.3 to 1-fold by weight, based on the amount of cyclohexanone oxime in the bottom product 16. The extraction temperature is usually selected from a range of a normal temperature to the boiling point of the organic solvent 17 and is preferably within a range of 40° C. to 90° C. The extractor 3 may be one by which multi-stage extraction can be carried out, or a single-stage or multi-stage mixer settler type extractor in which a mixing portion and a liquid/liquid-separation portion are separated.

The organic layer 18 from the extractor 3 is introduced in a washer 4 followed by being mixed with water 20, and then a mixture is separated into an organic layer 21 which is obtained by removing impurities from the organic layer 18 by washing with water and an aqueous layer 22 in which the impurities are dissolved (the washing step (4)). The impurities include, for example, ammonium nitrate, ammonium nitrite and the like which are yielded as by-products in the reaction step (1). The amount of water 20 used for washing is usually from 0.05 to 1-fold by weight based on the weight of cyclohexanone oxime in the organic layer 18, and the washing temperature is usually within a range of 40° C. to 90° C. Further, the washer 4 may be one by which multi-stages extraction can be carried out, or a single-stage or multi-stage mixer settler type extractor in which a mixing portion and a liquid/liquid-separation portion are separated, similarly to the extractor 3.

The organic layer 21 from the washer 4 is introduced into a second distillation column 5 to be subjected to distillation, such that the organic solvent in the organic layer 21 can be collected as a distillate 23 and the crude cyclohexanone oxime containing the above-mentioned unreacted cyclohexanone can be obtained as the bottom product 24 (the second distillation step (5)). In this step, water dissolved and/or dispersed in the organic layer 21 is collected as the distillate 23 together with the organic solvent. The distillation is usually carried out at a pressure between a normal pressure and a slightly reduced pressure depending on the boiling point of the organic solvent.

It is desirable that the organic solvent and water which are collected as the distillate 23 are recycled as the organic solvent 17 for extraction which is introduced in the extractor 3 and water 20 for washing which is introduced in the washer 4, respectively. Specifically, the organic solvent and water which are collected as the distillate 23 are introduced in a liquid/liquid separator 7 to be separated into the organic layer 17 and the aqueous layer 20, and then the organic layer 17 is introduced in the extractor 3, and the aqueous layer 20 is introduced in the washer 4.

One or two or more kinds of a compound 27 selected from an oxide, an oxo acid, an oxo acid salt, an oxo acid ester and an oxo acid amide of boron or phosphorous is/are added to the water 20 to be introduced to the washer 4 for washing the organic layer 18 from the extractor 3 in the above-mentioned washing step (4), and/or the organic layer 21 to be introduced to the second distillation tower 5 from the washer 4 to be distilled in the above-mentioned second distillation step (5). Where necessary, the compound can be added in the form of a solution or suspension in water or an organic solvent.

Examples of the oxide of boron may include diboron trioxide ($B_2O_3$) and the like, and examples of the oxo acid of boron may include orthoborate ($H_3BO_3$), metaborate ($HBO_2$), hypoborate ($H_4B_2O_4$) and the like, and condensed acids thereof. Where necessary, these oxides and oxo axids of boron may include elements other than boron and oxygen in the skeleton.

Examples of the oxide of phosphorous may include tetraphosphorous hexaoxide ($P_4O_6$; also referred to phosphorous trioxide) and tetraphosphorous decaoxide ($P_4O_{10}$; also referred to phosphorous pentaoxide), and examples of the oxo acid of phosphorous may include orthophosphorate ($H_3PO_4$), metaphosphate ($HPO_3$), phosphonic acid ($H_3PO_3$; also referred to as phosphorous acid) and phosphinic acid ($H_3PO_2$; also referred to as hypophosphorous acid), and condensed acids thereof. Where necessary, these oxides and oxo acids of phosphorous may include elements other than phosphorous and oxygen in the skeleton.

The oxo acid salts of boron or phosphorous may be a normal salt in which all protons of the oxo acid have been substituted with metal ions or ammonium ions, or an acidic salt in which some protons have been substituted with metal ions or ammonium ions. Preferable examples of the metal ion may include ions of metals of Group I (Group IA) of the periodic table such as sodium and potassium, metals of Group II (Group IIA) of the periodic table such as calcium and magnesium, metals of Group IV (Group IVA) of the periodic table such as titanium and zirconium, and metals of Group XII (Group IIB) of the periodic table such as zinc. Examples of ammonium ion may be those obtained by protonation of ammonia, those obtained by protonation of primary, secondary or tertiary aliphatic, alicyclic or aromatic amines, or quaternary ammonium ions.

Examples of the oxo acid ester of boron or phosphorous may be those in which all hydroxyl groups of an oxo acid have been substituted with alcohol residues (groups obtained by removing hydrogen atoms attached to the oxygen atoms of alcohol molecules) or those in which some hydroxyl groups have been substituted with alcohol residues. Similarly, examples of the oxo acid amide of boron or phosphorous may be those in which all hydroxyl groups of an oxo acid have been substituted with amine residues (groups obtained by removing hydrogen atoms attached to the nitrogen atoms of amine molecules) or those in which some hydroxyl groups have been substituted with amine residues. Examples of the alcohol residue for the oxo acid ester may be residues of primary, secondary or tertiary aliphatic, alicyclic or aromatic alcohols. Examples of the amine residue for the oxo acid amide may be residues of primary or secondary aliphatic, alicyclic or aromatic amines.

When the compound 27 of boron or phosphorous is added to the water 20, i.e., when the organic layer 18 from the extractor 3 is washed with an aqueous solution of the compound 27 in the washer 4, the amount of the compound 27 to be added is generally 0.01 to 3 mol/l, preferably 0.05 to 2 mol/l represented by the concentration in an aqueous liquid (the water 20 and the compound 27). When the compound 27 of boron or phosphorous is added to the organic layer 21, i.e., when the organic layer 21 from the washer 4 is distilled with addition of the compound 27 in the second distillation layer 5, the amount of the compound 27 to be added is generally 0.1 mol ppm to 1 mol %, preferably 0.5 mol ppm to 0.1 mol % relative to the cyclohexanone oxime included in the organic layer 21.

The crude cyclohexanone oxime which has been drawn as the bottom product 24 from the second distillation column 5 is introduced into a third distillation column 6 to be subjected to distillation such that the cyclohexanone can be collected as a distillate 25 and purified cyclohexanone oxime which contains no or reduced amount of cyclohexanone can be obtained as a bottom product 26 (the third distillation step (6)). The distillation is usually carried out at a temperature of 140° C. or less under reduced pressure of 10 kPa or less. Since the purified cyclohexanone oxime thus obtained is superior in thermal stability, it can be preferably used as a raw material for the gas phase Beckmann rearrangement. It is desirable that the distillation conditions are adjusted so that the concentration of cyclohexanone in said purified cyclohexanone oxime is 1% by weight or less and preferably 0.5% by weight or less from the viewpoint of suppressing a side reaction in the gas phase Beckmann rearrangement.

It is desirable to recycle cyclohexanone which is collected as the distillate 25 to the reaction vessel 1. Further, when the accumulation of impurities in the distillate 25 is remarkable because of operation for a long term and the like, at least a potion of the distillate may be purified by rectification or the like.

Further, it is desirable in order to reduce a loss of cyclohexanone oxime in the above process that cyclohexanone oxime which is contained in a very small amount in the aqueous layer discharged in the extraction step (3) and the aqueous layer discharged in the washing step (4) is extracted with an organic solvent to be collected. The organic solvent used here may be the same one as the organic solvent used in the extraction step (3). Accordingly, it is desirable that the organic solvent which is to be used in the extraction step (3) is firstly used for collecting a very small amount of cyclohexanone oxime from the above-mentioned aqueous layers, and then used in the extraction step (3). Further, the collection of cyclohexanone oxime is desirably carried out by multi-stage extraction.

Figure 2:
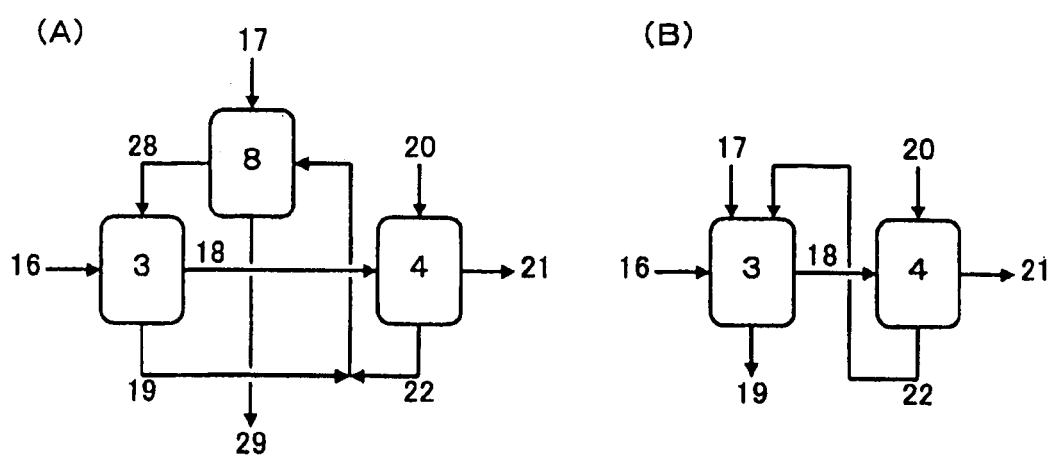
FIG. 2 is a flow chart schematically showing two examples of a step of collecting cyclohexanone oxime from water layers from the extraction step (3) and the washing step (4).

Specifically, as shown in FIG. 2(A), the aqueous layer 19 from the extractor 3 and the aqueous layer 22 from the washer 4 are introduced in a collector 8, mixed with the organic solvent 17, and separated into an organic layer 28 and an aqueous layer 29. The organic layer 28 contains a very small amount of cyclohexanone oxime which has been extracted from the water layer 19 and the aqueous layer 22 with the organic solvent 17. The aqueous layer 29 is a raffinate of extraction. The organic layer 28 is introduced in the extractor 3 and used as the organic solvent for extracting cyclohexanone oxime from the bottom product 16 of the first distillation column 2. Further, the aqueous layer 29 is treated as waste water. As the organic solvent 17 which is introduced in the collector 8, the organic layer 17 obtained from the distillate 23 from the second distillation column 5 may be used. Further, the collector 8 may be one by which multi-stage extraction can be carried out, or a single-stage or multi-stage mixer settler type extractor in which a mixing portion and a liquid/liquid-separation portion are separated, similarly to the extractor 3 and the washer 4.

Further, the aqueous layer discharged in the washing step (4) is advantageously subjected to the extraction step (3) together with the mixed solution of cyclohexanone oxime and water which is the bottom product of the first distillation step (2), in order to collect cyclohexanone oxime contained in a very small amount in the aqueous layer. In that case, the extraction step (3) is more advantageously carried out by multi-stage extraction, because the aqueous layer discharged from such an extraction step (3) can become an aqueous layer not substantially containing cyclohexanone oxime which is not required to be subjected to a collection treatment. Specifically, as shown in FIG. 2(B), the extraction step can be carried out by returning the water layer 22 from the washer 4 to the extractor 3 and mixing the water layer with the bottom 16 from the first distillation column 2 and the organic solvent 17, and separating the mixture into the organic layer 18 resulted from extraction of cyclohexanone oxime and cyclohexanone in the bottom 16 and a slight amount of cyclohexanone oxime in the water layer 22 with the organic solvent 17 and the water layer 19 which is extraction residue. The water layer 19 can be treated as waste water.

EXAMPLES

The present invention is described by some examples, but it is not limited to these examples. In Example, "%" representing the content is based on weight unless otherwise noticed.

Example 1

The respective steps and thermal stability test were carried out by applying the collection operations shown in FIG. 2(A) to the continuous production process shown in FIG. 1.

[The Reaction Step (1)]

A reaction solution in which the titanosilicate catalyst was dispersed was hold in a stirring vessel-type reaction vessel 1, and reaction was carried out by drawing a reaction solution 14 through a filter while feeding cyclohexanone 11, 60% hydrogen peroxide aqueous solution 12, ammonia 13 and tert-butyl alcohol containing water in an amount of 15% by weight into the vessel. The reaction was carried out at 85° C. and a pressure of 0.25 MPa (gauge pressure) under a feed molar ratio of cyclohexanone/hydrogen peroxide/ammonia/water/tert-butyl alcohol=1/1.1/1.8/4.29/4.0. Nitrogen gas which was yielded as a by-product in the reaction was removed out of the system, and ammonia gas which accompanied the nitrogen gas was absorbed in water to be collected. The concentrations of components in the reaction solution 14 were 20.43% of cyclohexanone oxime, 22.13% of water, 2.32% of ammonia, 0.10% of cyclohexanone and 52.32% of tert-butyl alcohol.

[The First Distillation Step (2)]

The reaction solution 14 which was drawn from the reaction vessel 1 was introduced into a first distillation column 2 together with the above-mentioned water wherein ammonia was absorbed, and subjected to distillation at a temperature of 83° C. and a pressure of 50 kPa (gauge pressure) such that ammonia and water-containing tert-butyl alcohol were collected as a distillate 15 and a mixture consisting of 47.97% of cyclohexanone oxime, 51.20% of water and 0.317% of cyclohexanone was obtained as a bottom product 16. The distillate 15 was used as a portion of ammonia which was fed to the reaction vessel 1 and the 15% water-containing t-butyl alcohol.

[Extraction Step (3)]

The bottom product 16 from the first distillation column 2 and toluene 28 whose weight was the same as that of cyclohexanone oxime contained in said bottom product 16 were introduced in an extractor 3, and the mixture was stirred at about 72° C. and then separated into a toluene layer 18 and an aqueous layer 19.

[The First Washing Step (4)]

The toluene layer 18 from the extractor 3 and water 20 whose amount was the same in weight as that of cyclohexanone oxime contained in said toluene layer 18 were introduced in a washer 4, and the mixture was stirred at about 72° C. and then separated into a toluene layer 21 and an aqueous layer 22.

[Oxime Collection Step]

The aqueous layer 19 from the extractor 3 and the aqueous layer 22 from the washer 4 were mixed, the mixed aqueous layer and toluene 17 were introduced in a collector 8. The mixture was stirred at about 72° C. and then separated into a toluene layer 28 and an aqueous layer 29. The toluene layer 28 was used as toluene 28 which was introduced in the extractor 3.

[The Second Distillation Step (5)]

To the toluene layer 21 from the washer 4 was added a solution of orthophosphate (3 mol ppm relative to the cyclohexanone oxime contained in the toluene layer 21) in a small amount of water. The mixture was introduced into a second distillation column 5, subjected to distillation under reduced pressure of 30 kPa at a temperature of 107° C. and such that a mixture of toluene and water was collected as a distillate 23 and crude cyclohexanone oxime with a purity of 98.10% which contained 1.077% of cyclohexanone was obtained as the bottom product 24. The distillate 23 was introduced in a liquid-liquid separator 7 and separated into a toluene layer 17 and an aqueous layer 20 at about 35° C. The toluene layer 17 was used as the toluene 17 which was introduced in the collector 8 and the aqueous layer 20 was used as the water 20 which was introduced in the washer 4.

[The Third Distillation Step (6)]

The bottom product 24 from the second distillation column 5 was introduced into a third distillation column 6, and subjected to distillation under reduced pressure of 4 kPa at a temperature of 120° C. such that cyclohexanone was collected as a distillate 25 and purified cyclohexanone oxime with a purity of 99.78% which contained 0.04% of cyclohexanone was obtained as a bottom product 26. The distillate 25 was used as a portion of cyclohexanone which was fed to the reaction vessel 1.

[Thermal Stability Test]

The purified cyclohexanone oxime which was obtained as the bottom product 26 was subjected to reduced pressure distillation at a temperature of 120° C. and under a pressure of 15 torr (2 kPa) until the distillate was not observed. The amount of residual tar was 0.01% based on the charge fed to distillation (this tar amount corresponded to the amount of tar before heating treatment). Further, the cyclohexanone oxime was subjected to heating treatment at a temperature of 200° C. under nitrogen gas flow for 5 hours, and then it was subjected to distillation under reduced pressure in the same manner as in the above-mentioned reduced pressure distillation. The amount of residual tar was 0.12% based on the charge fed to the distillation (this tar amount corresponded to the amount of tar after heating treatment). The increment of tar due to the heating treatment was 0.11%.

Comparative Example 1

Purified cyclohexanone oxime having the purity of 99.23% (including 0.01% of cyclohexanone) was obtained as the bottom 26 from the third distillation column 5, according to similar operations to those of Example 1 except that orthophosphate was not added to the toluene layer from the washer 4 to be introduced to the second distillation column 5 in the second distillation step (5). The thermal stability test was carried out in the same manner as in Example 1 with respect to the cyclohexanone oxime obtained. The amount of tar was 0.02% before heating treatment, the amount of tar was 1.80% after heating treatment, and the increment of tar due to the heating treatment was 1.78%.

As described above, the present invention provides, as a first embodiment, a process for producing cyclohexanone oxime including the following steps (1) to (6):

(1) reaction step: a step of reacting cyclohexanone, hydrogen peroxide and ammonia in the presence of a titanosilicate catalyst to give a reaction solution containing cyclohexanone oxime, water, unreacted ammonia and unreacted cyclohexanone, (2) first distillation step: a step of subjecting the reaction solution obtained in the step (1) to distillation to distil off ammonia and obtain a bottom product containing cyclohexanone oxime, water and cyclohexanone, (3) extraction step: a step of mixing the bottom product obtained in the step (2) with an organic solvent followed by separating a mixture into an organic layer and an aqueous layer, (4) washing step: a step of mixing the organic layer obtained in the step (3) with water followed by separating a mixture into an organic layer and an aqueous layer, (5) second distillation step: a step of subjecting the organic layer obtained in the step (4) to distillation to distill off the organic solvent and water and to obtain a bottom product containing cyclohexanone oxime and cyclohexanone, and (6) third distillation step: a step of subjecting the bottom product obtained in the step (5) to distillation to distil off cyclohexanone and to obtain a bottom product containing cyclohexanone oxime;

wherein a compound selected from an oxide, an oxo acid, an oxo acid salt, an oxo acid ester and an oxo acid amide of boron or phosphorous is added to at least one of the water used in the step (4) and the organic layer obtained in the step (4) to be subjected to the step (5).

The present invention provides, as a second embodiment, the process for producing cyclohexanone oxime according to the first embodiment, wherein the organic solvent used in the step (3) is one or more solvents selected from a hydrocarbon solvent, an ether solvent, and an ester solvent.

The present invention provides, as a third embodiment, the process for producing cyclohexanone oxime according to the first or the second embodiment, wherein the ammonia distilled off in the step (2) is recycled to the step (1).

The present invention provides, as a fourth embodiment, the process for producing cyclohexanone oxime according to any one of the first to the third embodiments, wherein the organic solvent distilled off in the step (5) is recycled to the step (3).

The present invention provides, as a fifth embodiment, the process for producing cyclohexanone oxime according to any one of the first to the fourth embodiments, wherein the water distilled off in the step (5) is recycled to the step (4).

The present invention provides, as a sixth embodiment, the process for producing cyclohexanone oxime according to any one of the first to the fifth embodiments, wherein the cyclohexanone distilled off in the step (6) is recycled to the step (1).

What is claimed is:

1. A process for producing cyclohexanone oxime including the following steps (1) to (6):
   (1) reaction step: a step of reacting cyclohexanone, hydrogen peroxide and ammonia in the presence of a titanosilicate catalyst to give a reaction solution containing cyclohexanone oxime, water, unreacted ammonia and unreacted cyclohexanone,
   (2) first distillation step: a step of subjecting the reaction solution obtained in the step (1) to distillation to distill off ammonia and obtain a bottom product containing cyclohexanone oxime, water and cyclohexanone,
   (3) extraction step: a step of mixing the bottom product obtained in the step (2) with an organic solvent followed by separating a mixture into an organic layer and an aqueous layer,
   (4) washing step: a step of mixing the organic layer obtained in the step (3) with water followed by separating a mixture into an organic layer and an aqueous layer,
   (5) second distillation step: a step of subjecting the organic layer obtained in the step (4) to distillation to distill off the organic solvent and water and to obtain a bottom product containing cyclohexanone oxime and cyclohexanone, and
   (6) third distillation step: a step of subjecting the bottom product obtained in the step (5) to distillation to distill off cyclohexanone and to obtain a bottom product containing cyclohexanone oxime;
   wherein a compound selected from an oxide, an oxo acid, an oxo acid salt, an oxo acid ester and an oxo acid amide of boron or phosphorous is added to at least one of the water used in the step (4) and the organic layer obtained in the step (4) to be subjected to the step (5).

2. The process according to claim 1, wherein the organic solvent used in the step (3) is one or more solvents selected from a hydrocarbon solvent, an ether solvent, and an ester solvent.

3. The process according to claim 1, wherein the ammonia distilled off in the step (2) is recycled to the step (1).

4. The process according to claim 1, wherein the organic solvent distilled off in the step (5) is recycled to the step (3).

5. The process according to claim 1, wherein the water distilled off in the step (5) is recycled to the step (4).

6. The process according to claim 1, wherein the cyclohexanone distilled off in the step (6) is recycled to the step (1).

* * * * *